United States Patent [19]

Bonfield et al.

[11] Patent Number: 4,705,904
[45] Date of Patent: Nov. 10, 1987

[54] VAPOR PHASE SYNTHESIS OF HEXAFLUOROISOBUTYLENE

[75] Inventors: John H. Bonfield, Basking Ridge; Harry E. Ulmer, Morristown, both of N.J.

[73] Assignee: Allied Corporation, Morris Township, Morris County, N.J.

[21] Appl. No.: 820,896

[22] Filed: Jan. 17, 1986

Related U.S. Application Data

[63] Continuation of Ser. No. 580,083, Feb. 14, 1984, abandoned.

[51] Int. Cl.$^4$ ............................................. C07C 17/26
[52] U.S. Cl. ..................................... 570/142; 570/153
[58] Field of Search .................. 580/83; 570/153, 142; 568/399, 407, 400, 384; 549/523

[56] References Cited

U.S. PATENT DOCUMENTS

| | | | |
|---|---|---|---|
| 3,332,965 | 7/1967 | Fukui et al. | 549/523 |
| 3,894,097 | 7/1975 | Vanderkooi et al. | 570/142 |
| 3,946,081 | 3/1976 | Wedemeyer et al. | 568/400 |
| 4,057,584 | 11/1977 | Torizuka et al. | 568/400 |
| 4,400,546 | 8/1983 | Rammelt et al. | 570/142 |

FOREIGN PATENT DOCUMENTS

| | | | |
|---|---|---|---|
| 62131 | 4/1983 | Japan | 568/384 |
| 2119800 | 11/1983 | United Kingdom | 570/153 |

Primary Examiner—Donald B. Moyer
Assistant Examiner—Joseph A. Boska
Attorney, Agent, or Firm—Richard C. Stewart; Gerhard H. Fuchs

[57] ABSTRACT

A vapor phase synthesis of hexafluoroisobutylene, which comprises contacting in the vapor phase in a catalyst zone, B, of a reactor hexafluoropropylene oxide with a fluorinated catalyst such as fluorinated silica-alumina at a temperature of about 400°–600° C. for a residence time sufficient to form a vapor stream comprising hexafluoroacetone which is thereafter directly contacted in a heating zone of the reactor with a vapor stream comprising a keytone-generating compound such as acetic anhydride at a temperature of about 500°–700° C. for a residence time sufficient to form a stream comprising hexafluoroisobutylene, substantially-free of perfluoroisobutylene and recovering the hexafluoroisobutylene product is disclosed. A direct one reactor vapor phase synthesis of hexafluoroisobutylene which comprises (a) contacting, in the vapor phase, hexafluoropropene with less than a stoichiometric amount of oxygen required to convert substantially all the hexafluoroisopropene into hexafluoropropylene oxide in the presence of a fluorinated catalyst such as fluorinated silica-alumina at a temperature of about 400°–600° C. for a time sufficient to form a vapor stream comprising hexafluoropropylene oxide substantially-free of oxygen; (b) directly contacting said vapor stream, in a catalyst zone, B, containing a fluorinated catalyst which is preferably the same as used in catalyst zone, A, at a temperature of about 400°–650°, preferably about 500°–650° C. for a time sufficient to form a vapor stream comprising hexafluoroacetone; (c) directly contacting the vapor stream comprising hexafluroacetone with a vaporized compound such as acetic anhydride at a temperature of about 500°–700° C., preferably about 600° C. for a time sufficient to form a vapor stream comprising hexafluoroisobutylene, substantially-free of perfluoroisobutylene; and (d) recovering hexafluoroisobutylene is also disclosed.

4 Claims, No Drawings

VAPOR PHASE SYNTHESIS OF HEXAFLUOROISOBUTYLENE

This application is a continuation of application Ser. No. 580,083 filed Feb. 14, 1984.

BACKGROUND OF THE INVENTION

1. Field of the Invention

The present invention relates to a vapor phase synthesis of hexafluoroisobutylene directly from hexafluoropropylene oxide. The present invention also relates to a vapor phase synthesis of hexafluoroisobutylene directly from hexafluoropropene.

2. Description of the Prior Art

Hexafluoroisobutylene is a known compound which is known to be useful for a variety of purposes such as, for example, a comonomer which forms polymers of exceptional thermal, chemical and mechanical properties with other comonomers such as vinylidene fluoride. The preparation of such copolymers is described in U.S. Pat. No. 3,706,723 to Chandrasekeran et al., issued Dec. 19, 1972.

Hexafluoroisobutylene has been previously prepared by methods which include the reaction of hexafluoroacetone with ketene (U.S. Pat. No. 3,894,097 to N. Vanderkooi), the reaction of hexafluorothioacetone with ketene or a ketene-generating compound (U.S. Pat. No. 4,244,891 to Van Der Puy et al.), the reaction of antimony trifluorodichloride with a chlorofluoroisobutylene [R. N. Hazeldine, J. Chem. Soc., 3565 (1953)] and the dehydration of hexafluoro-2-methyl-2-propanol with phosphorus pentachlordie [M. H. Kaufman et al., J. Org. Chem. 31, 3090 (1966)]or with sulfur tetrafluoride (E. E. Gilbert et al. in U.S. Pat. No. 3,656,786). See also U.S. Pat. No. 4,367,394 (Anello) which discloses a liquid phase synthesis of hexafluoroisobutylene starting from hexafluoropropene, elemental sulfur, and alkali metal fluoride in an aprotic solvent.

U.S. Pat. No. 4,165,340 (Tohzuka et al.) discloses a process for preparing hexafluoropropanone-2 from hexafluropropene by one step reaction which comprises contacting hexafluoropropene and oxygen with a fluorinated alumina or a fluorinated silica-alumina as a catalyst in the presence or absence of water, provided that water is present when the catalyst is the fluorinated alumina. See also U.S. Pat. Nos. 4,284,822 and 4,057,584 also to Tohzuka et al.

U.S. Pat. No. 3,600,409 (Milian et al.) discloses a process for oxidation of hexafluoropropene to hexafluoropropylene epoxide, which operates in the presence of an inert aromatic compound to eliminate the formation of hexafluoroacetone.

These preparations and others suffer trom one or more disadvantages from a commercial standpoint. For example, although the preparation involving hexafluoroacetone is a high-yield process, hexafluoroacetone represents a starting material of high cost, high toxicity and limited availability. The chlorofluoroisobutylene route involves several steps including a slow dehydrochlorination step, while the dehydration of the fluorinated tertiary butyl alcohol requires excessively long reaction times or expensive reagents The reaction of hexafluorothioacetone with ketene operates in the gas phase at elevated temperature (300°–800° C.) and requires special precautions for handling and preparing hexafluorothioacetone.

It is accordingly an object of the invention to provide a new one stage route to hexafluoroisobutylene which utilizes cheaper and more readily accessible starting materials and which operates without isolation of toxic intermediates.

Other objects and advantages of the invention will become apparent from the following description.

SUMMARY OF THE INVENTION

In accordance with one form of the invention there is provided a process for which comprises (a) contacting, in a catalyst zone B of a reactor, in the vapor phase, a stream comprising hexafluoropropylene oxide with a fluorinated catalyst at a temperature in the range of about 400° to about 650° C. for a residence time sufficient to form a vapor stream comprising hexafluoroacetone;

(b) directly contacting in a heating zone of the reactor, in the vapor phase the vapor stream comprising hexafluoroacetone with a compound selected from tne group consisting of acetic anhydride, acetone, acetic acid, isopropenyl acetate, acetylacetone, diketene and mixtures thereof, at a temperature in the range of about 500° to about 700° for a residence time sufficient to form a stream comprising hexafluoroisobutylene, substantially free of perfluoroisobutylene; and (c) recovering hexafluoroisobutylene product. In accordance with another form of the invention there is provided a process for converting hexafluoropropylene directly into hexafluoroisobutylene which consists essentially of:

(a) contacting, in catalyst zone A of the reactor, in the vapor phase, a stream comprising hexafluoropropene with less than a stoichiometric amount of oxygen gas required to convert substantially all hexafluoropropene into hexafluoropropylene oxide in the presence of a fluorinated catalyst at a temperature in the range of about 400° to about 600° C. for a residence time sufficient to form a vapor stream comprising hexafluoropropylene oxide substantial free of oxygen;

(b) contacting in a catalyst zone B of a reactor, in the vapor phase, the stream comprising hexafluoropropylene oxide with a fluorinated catalyst at a temperature in the range of about 400° to about 600° C. for a residence time sufficient to form a vapor stream comprising hexafluoroacetone;

(c) directly contacting in a heating zone of the reactor, in the vapor phase, the vapor stream comprising hexafluoroacetone with a compound selected from the group consisting of acetic anhydride, acetone, acetic acid, isopropenyl acetate, acetylacetone, diketene and mixtures thereof, at a temperature in the range of about 500° to about 700° for a residence time sufficient to form a stream comprising hexafluoroisobutylene, substantially free of perfluoroisobutylene; and (d) recovering hexafluoroisobutylene product.

DETAILED DESCRIPTION OF THE INVENTION

The present invention provides a single stage process for the preparation of hexafluoroisobutylene, substantially free of perfluoroisobutylene, starting from hexafluoropropylene oxide or hexafluoropropene without isolation and/or purification intermediate products such as hexafluoroacetone, a highly toxic substance. Hexafluoropropylene oxide may be prepared from hexafluoropropene (which is commercially available) by the procedure described in U.S. Pat. No. 3,600,409 (Milian et al.) Hexafluoroisobutylene prepared either from hexafluoropropene and oxygen or from hexafluoropropylene oxide is recovered in high yield and high purity and substantially free of perfluoroisobutylene, a highly toxic chemical.

In the form of the present invention starting from hexafluoropropylene oxide, a vapor stream of hexafluoropropylene oxide is fed at any convenient flow rate, e.g., in the range of about 0.04 to about 0.06 g-mole/hr to a reactor maintained at a temperature in the range of about 400° to about 650° C. and containing a fluorinated catalyst (hereinafter described) for a residence time sufficient to for a vapor stream comprising hexafluoroacetone which is not isolated but forwarded directly to a heating zone of the reactor for conversion to hexafluoroisobutylene.

The fluorinated catalyst in catalyst zone B (anc in catalyst zone A) is a member selected from the group consisting of fluorinated alumina, fluorinated silicaalumina, alakali metal fluoride, especially KF, on an activated alumina support. The preparation of activated alumina, fluorinated alumina and fluorinated silicaalumina is described in U.S. Pat. No. 4,165,340 which is hereby incorporated by reference.

When the catalyst is fluorinated alumina the presence of water in the reaction system is preferred to maintain a high selectivity of hexafluoropropene to hexafluoropropanone-2 for a long period of time. The introduction of water to the reaction system may be effected at any stage of the contact, e.g. from the initial stage of the contact or in the course of the contact. Further, it may be carried out continuously or discontinuously. The amount of water to be present in the reaction system may be usually not less than about 0.001 mol, preferably from about 0.001 to 0.03 mol, per 1 mol of hexafluoropropene.

The residence time in catalyst zone B (and in zone A) is not critical. Residence times in the range of about 10 seconds to about 500 seconds are conveniently employed but longer or shorter residence times may be used depending on the flow rates, volume of catalyst and reactor design.

The pressure in the catalyst zone B (and in zone A) is not critical. Atmospheric, subatmospheric and superatmospheric pressures (up to 5 kg/cm2) may be employed. When superatmospheric pressures are employed in the catalyst zone (A and/or B), pressure let down to near atmospheric before the contact of hexafluoroacetone to hexafluoroisobutylene is desireable.

In the form of the present invention starting from hexafluoropropene, a vaporized admixture of hexafluoropropene and oxygen gas are fed to catalyst zone A maintained at a temperature in the range of about 400° to about 600° C. and containing a fluorinated catalyst described hereinabove; conveniently the same fluorinated catalyst is employed in zones A and B. It is critical feature of this form of the invention, that less than the stoichiometric amount of oxygen required to convert substantially all the hexafluoropropene into hexafluoropropylene oxide be present. Conveniently, about 0.05 to about 0.1 moles of oxygen gas per 0.5 moles of hexafluoropropene are fed to catalyst zone A. In catalyst zone B, the vaporized mixture of hexafluoropropylene oxide and unconverted hexafluoropropene is converted into hexafluoroacetone containing unreacted hexafluoropropene. Conversions in zone B are normally in the order of about 10%. Oxidative side products from zone A such as $CO_2$, COF, may also be present.

In both forms of the present invention, hexafluoroacetone is directly contacted in the vapor phase in a heating zone of the reactor with a compound selected from the group consisting of acetic anhydride, acetone, acetic acid, isopropenyl acetate, acetylacetone, diketene and mixtures thereof, at a temperature in the range of about 500° to about 700° for a residence time sufficient to form a stream comprising hexafluoroisobutylene, substantially-free of perfluoroisobutylene. All of the above-listed compounds generate ketene under the conditions maintained in the heating zone. Preferred ketene-generating compounds include acetic anhydride, acetone and acetic acid. Especially preferred as the starting reactant is acetic anhydride due to the resulting high yield (i.e., substantially quantitative) of the hexafluoroisobutylene product.

The ketene-generating compounds useful in the present invention are added, in the vapor state, conveniently at a point in heating zone of reactor closest to the interface of catalyst zone B and the heating zone. However, the preferred ketene-generation compounds, especially acetic anhydride may be also added, in the liquid state, near or at the interface point to hexafluoroacetone at a temperature of 500°-700° C.

The temperature in the heating zone is in the range of about 500°-700° C. preferably about 600° C. The pressure is not critical but near atmospheric pressures are especially desireable. The residence times in the heating zone are not critical. Conveniently residence times in the range of about 10 seconds to 10 minutes may be employed.

As the reactor, there can be employed any conventional reactions apparatus, such as a tube, vessel, etc. Since the reactions occur in the gas phase, a reaction tube has proven quite acceptable as the reaction chamber. The reaction tube or similar chamber may be formed of any conventional material capable of withstanding the reaction temperatures. These materials include metals such as copper and stainless steel, quartz, glass, heat-resistant glass, etc. It is not desireable, however, to employ reaction heating zone of the reactor formed of 316 stainless steel when the heating zone of the reactor is to be heated to temperatures above about 550° C. since such material tends to catalyze reactions which form methane, carbon monoxide and carbon rather than the desired product. The size of the reaction tube or vessel is dictated by the desired residence time, flow rates, etc. For example, the diameter of the reaction tube may range from about one-fourth to 4 inches with lengths in the range of 1 to 10 feet also possible.

In the form of the present invention starting from hexafluoropropene, per 0.5 mole of hexafluoropropene fed to the catalyst zone A of the reactor, about 0.4 moles of hexafluoropropene is recovered (by fractionation) for recycle and about 0.08 moles of hexafluoroisobutylene is recovered for a over all yield of 80%.

In both forms of the present invention hexafluoroisobutylene is obtained substantially-free of the highly toxic perfluoroisobutylene Conventional purification of the reaction mixture exiting from the heating zone of the reactor are employed to recover highly pure hexafluoroisobutylene, and hexafluoropropene for recycle.

EXAMPLE 1

A 316 SS stainless tube (1" ID by 12" long) was packed with 48 g of ⅛" activated alumina pellets (MCB type L-1151). At 200° C., hexafluoropropene (HFP) was passed over the catalyst for 4 hours at a rate of 0.04-0.06 g mole/hr. Again at the same, hexafluoropropene gas was passed at 200° C. for 4 hours. The reactor was then purged with $N_2$ gas. At 400° C., hexafluoroisopropylene oxide (HFPO) is then passed over the catalyst at a rate of 0.05 g mole/hr.

In this single stage case, the hexafluoroacetone (6FK) produced may be assayed by continuous adsorption in water. Hexafluoroacetone trihydrate (6FK.$3H_2O$) which was produced may then be determined by direct GLC analysis using an internal standard. Alternatively, 6FK.$3H_2$, may be determined by potentiometric titration against a standard NaOH. Titer to pH of 4 is due to hydrogenfluoride, if present; titer from pH of 4 to pH of 9 is due to 6FK.$3H_2O$. Optionally, the 6FK may be recovered by passage through a dry ice condensing system to give 6FK liquid (BP-28° C.).

EXAMPLE 2

Through tubular copper reactor (½" ID×12" long) held at 600° C. was passed 0.05 g-mole/hr of 6FK gas and 0.075 g-mole/hr of acetic anhydride which was fed as a liquid to the hot upstream end of the reactor. Residence time based on total gas volume at 600° C. was 16 sec. After cooling the product gas stream to 200° C. (water scrub), and liquidation in a dry ice condensor, liquid hexafluoroisobutylene (HFIB) (99% purity) was obtained at a rate of 0.045-0.048 g-mole/hr. The hot gas before water scrubbing was analyzed by GLC to have a 80% area % purity. The main impurities apart from acetic acid and $CO_2$, were $CF_3COF$ and some $C_2F_6$. No perfluoroisobutylene, $C_4F_8$, was detected.

EXAMPLE 3

The reactors described in Examples 1 and 2 were coupled together and run in accordance with procedures of Examples 1 and 2 with a hexafluoroiospropylene oxide fed to the first stage at a rate of 0.06 g-mole/hr; acetic anhydride was fed to the interstage at a rate of 0.07 g-mole/hr 0.05 g-mole/hr. Liquid hexafluoroisobutylene (99% purity) was collected after scrubbing and dry ice condensation. No perfluoroisobutylene was detected.

EXAMPLE 4

This example illustrates operation of the process of the present invention using HFP and $O_2$ as feed to the first zone, A, containing activated alumina. The alumina is activated as described in example 1 but the conditions are modified as follows.

After the HF gas treatment is performed as Example 1, HFP gas is fed at 0 5 g-mole/hr and the temperature is adjusted to control at 200° C. Pure $O_2$ gas admixed with the feed HFP such that there is always a moler deficiency thereof relative to HFP to be converted; 0.05 to 0.10 mole of $O_2$, per 0.5 mole of HFP is desirable Pressure may also be used, up to 5 kg/cm² in the first stage. In this event, however, pressure let down to near atmospheric between stages before injection of acetic anhydride is desireable. Conversion of HFP to 6FK in the first stage is of the order of 10%. Some oxidation side products such as $CO_2$, COF are present. It is believed, however, that there side products would not interfere with the conversion reaction of 6FK to HFIB.

After the gas from the second HFIB stage reaction is scrubbed in accordance with the procedure of Examples 1-3 HFIB is condensed, such as by vapor compression and cooling or directly by dry ice condensation. Fractionation then serves to readily separate unreacted HFP (boiling point - 29° C.) from HFIB (boiling point +12° C.). The HFP may be recycled to reaction

We claim:

1. A process for which comprises
   (a) contacting, in a catalyst zone B of a reactor, in the vapor phase, a stream comprising hexafluoropropylene oxide with a fluorinated catalyst selected from the group consisting of fluorinated alumina, fluorinated silica-alumina, alkali metal fluoride, on an activated alumina support and mixtures thereof at a temperature in the range of about 400° to about 650° C. for a residence time sufficient to form a vapor stream comprising hexafluroacetone;
   (b) directly contacting in a heating zone of the reactor, in the vapor phase the vapor stream comprising hexafluroroacetone with a compound selected from the group consisting of acetic anhydride, acetone, acetic acid, isopropenyl acetate, acetylacetone, diketene and mixtures thereof, at a temperature in the range of about 500° to about 700° for a residence time sufficient to form a stream comprising hexafluoroisobutylene substantially free of perfluoroisobutylene; and
   (c) recovering hexafluroroisobutylene product.

2. The process of claim 1 wherein the fluorinated catalyst in the catalyst zone is a member selected from group consisting of fluorinated alumina, fluorinated silica-alumina, alkali metal fluoride on an activated alumina support and mixtures thereof.

3. The process of claim 1 wherein a molar feed ratio of the compound of vapor stream comprising hexafluoroacetone is in the range of about 0.5:1 to about 4:1.

4. A process for coverting hexafluoropropylene directly into hexafluoroisobutylene which consists essentailly of:
   (a) contacting, in a catalyst zone A of the reactor, in the vapor phase, a stream comprising hexafluoropropene with les than a stoichiometric amount of oxygen gas required to convert substantially all hexafluoropropene into hexafluoropropylene oxide in the presence of a fluorinated catalyst selected from the group consisting of fluorinated alumina, fluorinated silica-alumina, alkali metal fluoride on an activated alumina support and mixtures thereof at a temperature in the range of about 400° to about 600° C. for a residence time sufficient to form a vapor stream comprising hexafluoropropylene oxide substantially free of oxygen;
   (b) contacting, in a catalyst zone B of a reactor, in the vapor phase, the stream comprising hexafluoropropylene oxide with a fluorinated catalyst selected from the group consisting of fluorinated alumina, fluorinated silica-alumina, alkali metal fluoride, on an activated alumina support and mixtures thereof at a temperature in the range of about 400° to about 600° for a residence time sufficient to form a vapor stream comprising hexafluoroacetone;
   (c) directly contacting in a heating zone of the reactor, in the vapor phase the vapor stream comprising hexafluoroacetone with a compound selected from the group consisting of acetic anhydride, acetone, acetic acid, isopropenyl acetate acetylacetone; diketene and mixtures thereof, at a temperature in the range of about 500° to about 700° for a residence time sufficient to form a stream comprising hexafluoroisobutylene, substantially-free of perfluoroisobutylene; and
   (d) recovering hexafluoroisobutylene product.

* * * * *